United States Patent

Arlt et al.

[11] 4,191,712
[45] Mar. 4, 1980

[54] PROCESS FOR THE PREPARATION OF 1,1-DIHALO-4-METHYL-1,3-PENTADIENE COMPOUNDS

[75] Inventors: Dieter Arlt, Cologne; Manfred Jautelat, Burscheid, both of Fed. Rep. of Germany

[73] Assignee: Bayer Aktiengesellschaft, Leverkusen, Fed. Rep. of Germany

[21] Appl. No.: 964,216

[22] Filed: Nov. 27, 1978

[30] Foreign Application Priority Data

Dec. 16, 1977 [DE] Fed. Rep. of Germany ....... 2756271

[51] Int. Cl.$^2$ ............................................. C07C 17/24
[52] U.S. Cl. ............................ 260/654 D; 260/654 R; 260/655
[58] Field of Search ................. 260/654 D, 654 R, 655

[56] References Cited

U.S. PATENT DOCUMENTS

| | | | |
|---|---|---|---|
| 4,053,380 | 10/1977 | Fujita et al. | 260/655 |
| 4,070,404 | 1/1978 | Lupichuk | 260/654 D |
| 4,078,008 | 3/1978 | Lantzsche et al. | 260/654 R |
| 4,081,488 | 3/1978 | Scharpf | 260/654 R |

OTHER PUBLICATIONS

Farkas et al., Coll. Czech. Chem. Comm. 24(1959), pp. 2230–2236.

*Primary Examiner*—Arthur P. Demers
*Attorney, Agent, or Firm*—Sprung, Felfe, Horn, Lynch & Kramer

[57] ABSTRACT

Process for making 1,1-dihalo-4-methyl-1,3-pentadiene compounds which process comprises reacting a 2-2-dimethyl-3,5,5,5-tetrahelogenopent-1-yl derivative of the formula

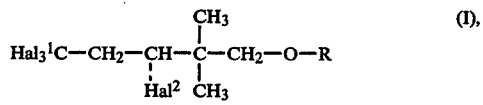

in which
Hal$^1$ is defined as above,
Hal$^2$ is halogen, and
R is hydrogen or alkanoyl of up to 5 carbon atoms with a substance having a basic reaction in a temperature range from 20° to 160° C. Certain intermediates produced in such process can also be used as the initial starting material.

14 Claims, No Drawings

PROCESS FOR THE PREPARATION OF 1,1-DIHALO-4-METHYL-1,3-PENTADIENE COMPOUNDS

The invention relates to a process for the preparation of certain 1,1-dihalogeno-4-methyl-1,3-pentadienes.

It is known to prepare 1,1-dichloro-4-methyl-1,3-pentadienes by reacting 1,1,1-trichloro-2-acetoxy-4-methyl-3-pentene with zinc dust and acetic acid (Coll. Czech. Chem. Commun. 24, 2,230 (1959)).

It is also known to obtain 1,1-dihalogeno-4-methyl-pentadienes by reacting isobutene with a 1,1,2-trihalogenoethylene in the vapour phase (DT-OS (German Published specification No.) 2,629,868).

Furthermore, it is known to obtain isomeric 1,1-dihalogeno-4-methyl-pentadienes by electrochemical reduction of isomeric 1,1,1-trihalogeno-2-hydroxy-4-methyl-pentenes (U.S. Pat. No. 4,022,672).

The present invention now provides a process for the preparation of a 1,1-dihalogeno-4-methyl-1,3-pentadiene. The process comprises reacting 2,2-dimethyl-3,5,5,5-tetrahalogeno-pent-1-yl derivative of the general formula

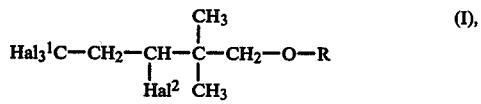

in which

Hal$^1$ represents halogen, the Hal$^1$ atoms being selected independently of one another, Hal$^2$ represents halogen, and R represents hydrogen or C$_1$-C$_5$-acyl, with a substance having a basic reaction, in the temperature range from 20° to 160° C., optionally in the presence of an inert diluent.

Examples of halogen atoms Hal$^1$ and Hal$^2$ which may be mentioned are fluorine, chlorine, bromine and iodine, preferably fluorine, chlorine and bromine and particularly preferably chlorine and bromine.

Examples of acyl radicals (R) which may be mentioned are those with 1–5 carbon atoms, for example formyl, acetyl, propionyl, butyryl, isobutyryl, valeroyl and isovaleroyl. Acyl radicals (R) with 1 to 3 carbon atoms are preferred, for example formyl, acetyl or propionyl. The acetyl radical is particularly preferred.

The 2,2-dimethyl-3,5,5,5-tetrahalogeno-pent-1-yl derivatives of the formula (I) can be prepared from the known 2,2-dimethyl-3-buten-1-ol derivatives (J. Org. Chem. 30, 10 (1965)) by adding on tetrahalogenomethanes in the presence of agents which form free radicals, which procedure is also known (J. Am. Chem. Soc. 69, 1,100 (1947)).

Examples which may be mentioned of starting materials which can be used according to the invention are: 2,2-dimethyl-3,5,5,5-tetrachloropentyl acetate, 2,2-dimethyl-3,5,5,5-tetrachloropentan-1-ol, 2,2-dimethyl-3,5,5,5-tetrabromopentyl acetate, 2,2-dimethyl-3,5,5,5-tetrabromopentan-1-ol, 3-bromo-2,2-dimethyl-5,5,5-trichloropentyl acetate, 3-bromo-2,2-dimethyl-5,5,5-trichloropentan-1-ol, 3-chloro-2,2-dimethyl-5,5,5-trifluoropentyl acetate, 3-chloro-2,2-dimethyl-5,5,5-trifluoropentan-1-ol, 2,2-dimethyl-3,5,5,5-tetrachloropentyl propionate, 2,2-dimethyl-3,5,5,5-tetrachloropentyl butyrate and 2,2-dimethyl-3,5,5,5-tetrachloropentyl valeroate.

Substances having a basic reaction used in the process according to the invention can belong to the group comprising tertiary amines, alkali metal hydroxides, alkali metal carbonates, alcoholates and amides. Examples of tertiary amines which can be employed are triethylamine, dimethyl-benzyl-amine, pyridine, ethyl-diisopropylamine, dimethylaniline, 1,8-diazabicyclo(5,4,0)-undec-7-ene, 1,5-diazabicyclo(4,3,0)-non-5-ene or triethylenediamine. Hydroxides of tertiary amines can also be used, for example by adding the appropriate amount of water to one of the possible tertiary amines. This procedure is particularly advantageous because it enables amines which still contain water from a preceding purification stage to be employed without first being dried.

Examples of alkali metal hydroxides which may be mentioned are sodium hydroxide or potassium hydroxide. Examples of alkali metal carbonates which may be mentioned are sodium carbonate or potassium carbonate. Examples of alcoholates which may be mentioned are sodium methylate, sodium ethylate or potassium tert.-butylate. Examples of amides which may be mentioned are sodium amide, potassium amide or lithium diisopropylamide.

Alkali metal hydroxides are preferably employed in the process according to the invention. Sodium hydroxide is very particularly preferably employed.

The starting material of the formula (I) and the substance having a basic reaction are generally employed in the molar ratio of 1:2 to 1:5, preferably 1:2.1 to 1:3.5.

The process according to the invention can be carried out with or without a diluent. It is appropriately carried out without a diluent if the starting materials are liquid.

Suitable diluents are organic and inorganic solvents which are inert under the reaction conditions. Inert organic solvents can belong to the group comprising hydrocarbons, for example benzine, cyclohexane or toluene, halogenated hydrocarbons, for example methylene chloride, 1,2-dichloroethane, chlorobenzene or dichlorobenzene, ethers, for example diethyl ether, tetrahydrofuran, dioxan or dimethoxyethane, and alcohols, for example methanol, ethanol, butanol or ethylene glycol. Examples of further inert organic solvents which may be mentioned are acetonitrile, dimethylsulphoxide, dimethylformamide or hexamethylphosphoric acid triamide.

Water may be mentioned as an example of an inert inorganic solvent.

A preferred process varient is to use water-containing solvents, and at the same time to use alkali metal hydroxides as the substances having a basic reaction. This variant has the advantage that organic solvents which are water-miscible can be employed without first being dried.

The process according to the invention can be illustrated by the equation which follows, using the reaction of 2,2-dimethyl-3,5,5,5-tetrachloropentyl acetate with sodium ethylate to give 1,1-dichloro-4-methyl-1,3-pentadiene as an example:

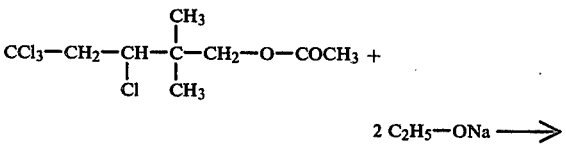

-continued

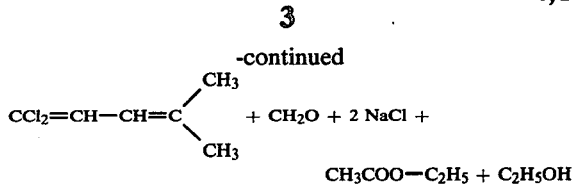

$$CH_3COO-C_2H_5 + C_2H_5OH$$

Possible intermediate stages of the process according to the invention, which in the case of a suitable reaction procedure are to be isolated or which can be prepared in another manner, can, of course, be employed in the process according to the invention instead of the starting materials. The following compounds, represented by their formulae, may be mentioned as examples of such possible intermediate stages, $Hal^1$, $Hal^2$ and R having the meanings indicated above:

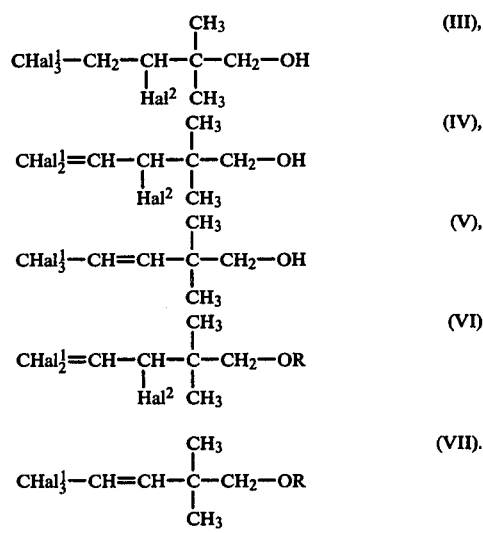

The process according to the invention can be carried out, for example, as follows:

The substance having a basic reaction and if appropriate the diluent are initially introduced and the starting material of the formula (I) is added at room temperature. The reaction mixture is then stirred. The reaction mixture is worked up by taking up in a suitable solvent, for example pentane or methylene chloride, then washing the mixture with water and subsequently distilling the product phase.

The 1,1-dihalogeno-4-methyl-1,3-pentadienes of the general formula

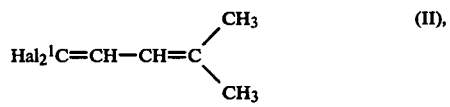

in which
$Hal^1$ represents halogen,
which can be prepared by the process according to the invention are known and can be used as intermediate products for the preparation of insecticides, such as, for example, 2-(2,2-dichlorovinyl)-3,3-dimethyl-cyclopropanecarboxylic acid and esters thereof (Coll. Czech. Chem. Commun. 24, 2,230 (1959)).

The preparative processes belonging to the state of the art and described above for the compounds of the formula (II) have the disadvantage that in some cases they proceed via numerous reaction stages (Coll. Czech. Chem. Commun. 24, 2,230 (1959) and DT-OS (German Published Specification) 2,629,868) and in some cases they give only low yields (U.S. Pat. No. 4,022,672). The process according to the invention avoids the disadvantages indicated by the fact that it gives high yields in a one-stage reaction from precursors which can be obtained in a simple manner.

It is to be described as decidedly surprising that in spite of the possible intermediate stages shown above, which in some cases can appear side by side and in other cases can appear successively, the process according to the invention leads to the reaction product of the formula (II) in high yield in a so-called "one-pot" reaction.

The process of the present invention is illustrated by the following Examples.

EXAMPLE 1 (Starting material)

16.5 g (0.116 mol) of 2,2-dimethyl-3-butenyl acetate (J. Org. Chem. 30, 10 (1965)) were heated under reflux in 120 ml of carbon tetrachloride, with the addition of 3.6 g of dibenzoyl peroxide, for 12 hours and the mixture was then distilled. 28.3 g (0.096 mol; 83% of theory) of 2,2-dimethyl-3,5,5,5-tetrachloropentyl acetate (melting point 56°–58° C.) were isolated at boiling point 96°–99° C./0.2 mm Hg.

EXAMPLE 2

29.6 g (0.1 mol) of 2,2-dimethyl-3,5,5,5-tetrachloropentyl acetate were added dropwise to a solution of 0.35 mol of sodium ethylate in 200 ml of absolute ethanol at room temperature and the mixture was then heated under reflux for 2 hours. The solution was diluted with n-pentane and filtered and the filtrate was extracted by washing with water. The pentane phase was dried and the pentane was distilled off over a column. The residue was fractionated and gave 12.7 g (0.084 mol; 84%) of 1,1-dichloro-4-methyl-1,3-pentadiene at boiling point 57°–59° C./13 mm Hg.

EXAMPLE 3 (STARTING MATERIAL)

10 g (0.1 mol) of 2,2-dimethyl-3-buten-1-ol were heated under reflux in 100 ml of carbon tetrachloride, with the addition of 2.4 g of dibenzoyl peroxide, for 21 hours. By distillation, 23.2 g (0.091 mol; 91%) of 2,2-dimethyl-3,5,5,5-tetrachloropentan-1-ol were obtained at boiling point 88°–92° C./0.1 mm Hg.

EXAMPLE 4

25.4 g (0.1 mol) of 2,2-dimethyl-3,5,5,5-tetrachloropentanol were heated under reflux in 140 ml of a 1.5 N sodium ethylate solution in ethanol for 8 hours. The mixture was worked up analogously to Example 2. After distillation, 13.9 g (0.092 mol; 92%) of 1,1-dichloro-4-methyl-1,3-pentadiene were isolated (boiling point: 58°–60° C./15 mm Hg).

EXAMPLE 5 (STARTING MATERIAL)

7.1 g (50 mmol) of 2,2-dimethyl-3-butenyl acetate and 16.6 g (50 mmol) of carbon tetrabromide were heated to 90° C., together with 0.5 g of dibenzoyl peroxide, for 5 hours. Distillation at boiling point: 120°–125° C./0.1 mm Hg gave 17.3 g (36.5 mmol; 73%) of 2,2-dimethyl-3,5,5,5-tetrabromopentyl acetate.

EXAMPLE 6

23.7 g (50 mmol) of 2,2-dimethyl-3,5,5,5-tetrabromopentyl acetate were heated under reflux with 160 mmol of sodium ethylate in 150 ml of ethanol for 6 hours. The solution was diluted with methylene chloride and extracted by shaking with water. After drying, the solution was distilled in vacuo. 10.6 g (44 mmol; 88%) of 1,1-dibromo-4-methyl-1,3-pentadiene were obtained at boiling point 89°–92°/20 mm Hg.

EXAMPLE 7

29.6 g (0.1 mol) of 2,2-dimethyl-3,5,5,5-tetrachloropentyl acetate were heated under reflux in 100 ml of methanol with 14 g (0.35 mol) of sodium hydroxide for 6 hours. The mixture was worked up analogously to Example 2 and gave 81% (of theory) of 1,1-dichloro-4-methyl-1,3-pentadiene.

EXAMPLE 8

29.6 g (0.1 mol) of 2,2-dimethyl-3,5,5,5-tetrachloropentyl acetate were heated under reflux with 12 g (0.3 mol) of sodium hydroxide in a mixture of 100 ml of water and 100 ml of dioxan for 8 hours. 78% (of theory) of 1,1-dichloro-4-methyl-1,3-pentadiene were isolated.

EXAMPLE 9

14.8 g (50 mmol) of 2,2-dimethyl-3,5,5,5-tetrachloropentyl acetate were heated under reflux with 22.8 g (150 mmol) of 1,8-diazabicyclo(5.4.0)-undec-7-ene (DBU) in 100 ml of ethanol for 4 hours. After cooling, the solution was diluted with water and extracted with n-pentane. After distilling off the solvent from the organic phase, further distillation gave 5.6 g (37 mmol, which corresponds to a yield of 74% of theory) of 1,1-dichloro-4-methyl-1,3-pentadiene (boiling point: 64°–67° C./20 mm Hg).

It will be understood that the specification and examples are illustrative but not limitative of the present invention and that other embodiments within the spirit and scope of the invention will suggest themselves to those skilled in the art.

What is claimed is:

1. Process for the preparation of a 1,1-dihalogeno-4-methyl-1,3-pentadiene of the formula

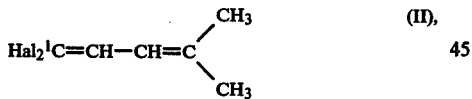

in which
Hal$^1$ is halogen, the two Hal$^1$ atoms being independent of one another
which process comprises reacting a 2,2-dimethyl-3,5,5,5-tetrahalogenopent-1-yl derivative of the formula

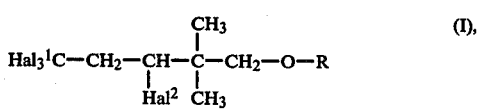

in which
Hal$^1$ is defined as above,
Hal$^2$ is halogen, and
R is hydrogen or alkanoyl of up to 5 carbon atoms with a substance having a basic reaction in a temperature range from 20° to 160° C.

2. Process as claimed in claim 1, wherein the process is carried out in the presence of an inert diluent.

3. Process as claimed in claim 1, wherein the raction is carried out in the temperature range from 50° to 120° C.

4. Process as claimed in claim 1, wherein the substance having a basic reaction is selected from alkali metal hydroxides, alkali metal carbonates, alcoholates, amides and tertiary amines.

5. Process as claimed in claim 3, wherein sodium hydroxide is employed as the substance having a basic reaction.

6. Process as claimed in claim 2, wherein a water-containing inert diluent is employed.

7. Process as claimed in claim 1, wherein the compound (I) and the substance having a basic reaction are employed in a molar ratio of 1:2 to 1:5.

8. Process as claimed in claim 7, wherein the compound (I) and the substance having a basic reaction are employed in a molar ratio of 1:2.1 to 1:3.5.

9. Process as claimed in claim 1, wherein Hal$^1$ and Hal$^2$ are selected from fluorine, bromine and chlorine atoms and R is hydrogen, formyl, acetyl or propionyl.

10. Process as claimed in claim 1, wherein the starting material is of the formula

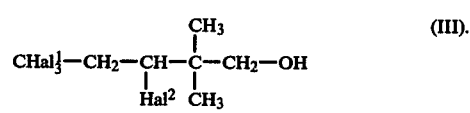

11. Process for the preparation of a 1,1-dihalogeno-4-methyl-1,3-pentadiene compound of the formula

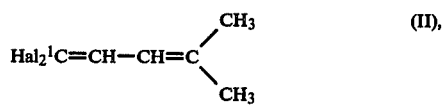

wherein
Hal$^1$ is halogen, the two Hal$^1$ atoms being selected independently of one another,
which process comprises reacting a compound of the formula

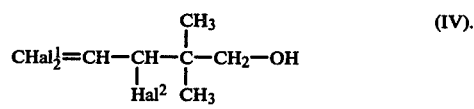

wherein
Hal$^1$ and Hal$^2$ are defined as above,
with a substance having a basic reaction in a temperature range from 20° to 160° C.

12. Process for the preparation of a 1,1-dihalogeno-4-methyl-1,3-pentadiene compound of the formula (II) which process comprises reacting a compound of the formula

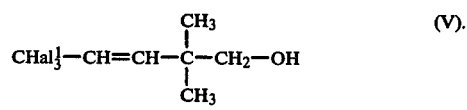

wherein
Hal$^1$ is halogen, the three Hal$^1$ atoms being selected independently of one another,
with a substance having a basic reaction in a temperature range from 20° to 160° C.

13. Process for the preparation of a 1,1-dihalogeno-4-methyl-1,3-pentadiene compound of the formula (II) which process comprises reacting a compound of the formula

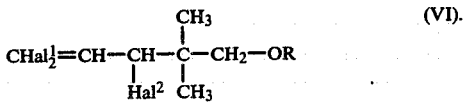 (VI).

wherein
Hal¹ and Hal² are independently selected halogen and
R is hydrogen or alkanoyl of up to 5 carbon atoms
with a substance having a basic reaction, in a temperature range from 20° to 160° C.

14. Process for the preparation of a 1,1-dihalogeno-4-methyl-1,3-pentadiene compound of the formula (II) which process comprises reacting a compound of the formula

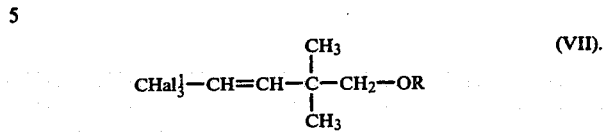 (VII).

wherein
Hal¹ is independently selected halogen and
R is hydrogen or alkanoyl of up to 5 carbon atoms
with a substance having a basic reaction, in temperature range from 20° to 160° C.

* * * * *